(12) United States Patent
Kohno et al.

(10) Patent No.: US 8,038,609 B2
(45) Date of Patent: Oct. 18, 2011

(54) ELECTRONIC ENDOSCOPE APPARATUS AND PROGRAM

(75) Inventors: Shinichi Kohno, Saitama (JP); Hiroshi Fujita, Saitama (JP); Daisuke Ayame, Saitama (JP)

(73) Assignee: Fujinon Corporation, Saitama-Shi (JP)

( * ) Notice: Subject to any disclaimer, the term of this patent is extended or adjusted under 35 U.S.C. 154(b) by 1237 days.

(21) Appl. No.: 11/730,094

(22) Filed: Mar. 29, 2007

(65) Prior Publication Data

US 2007/0232861 A1   Oct. 4, 2007

(30) Foreign Application Priority Data

Mar. 31, 2006   (JP) .................. 2006-098921

(51) Int. Cl.
*A61B 1/06* (2006.01)
(52) U.S. Cl. ..................................................... 600/160
(58) Field of Classification Search .......... 382/162–163; 600/160, 178
See application file for complete search history.

(56) References Cited

U.S. PATENT DOCUMENTS

| | | |
|---|---|---|
| 6,498,948 B1 | 12/2002 | Ozawa et al. |
| 6,668,185 B2 | 12/2003 | Toida |
| 2002/0051512 A1 | 5/2002 | Toida |
| 2002/0052547 A1 | 5/2002 | Toida |
| 2005/0185192 A1 | 8/2005 | Kim et al. |
| 2006/0183976 A1* | 8/2006 | Adler et al. .................. 600/176 |
| 2007/0153335 A1* | 7/2007 | Hosaka ......................... 358/463 |

OTHER PUBLICATIONS

A.M. Rollins et al., Optics Letters, vol. 24, No. 19, pp. 1358-1360 Mar. 31, 1999.

* cited by examiner

*Primary Examiner* — Philip Smith
(74) *Attorney, Agent, or Firm* — Birch, Stewart, Kolasch & Birch, LLP

(57) ABSTRACT

An endoscope apparatus used in combination with a near infrared light irradiation unit that irradiates near infrared light on a target irradiation section. White light and the infrared light are irradiated on a target observation area including the target irradiation section. The imaging means spectroscopically images a reflected light image of the target observation area, which is outputted as a spectral image signal. The storage section includes estimated matrix data. The IR image signal generation means generates an IR image signal constituted by an estimated value of reflected light intensity of the near infrared light by performing a matrix operation on the spectral image signal using the estimated matrix data and spectral matrix data of the near infrared light. The color image signal generation means generates a color image signal based on the spectral image signal and the IR image signal.

12 Claims, 9 Drawing Sheets

| | n=1 | n=2 | n=3 | n=4 | n=5 |
|---|---|---|---|---|---|
| m = 400 | 0.74 | 0.00 | 0.00 | 0.00 | 0.00 |
| 405 | 0.71 | 0.00 | 0.00 | 0.00 | 0.00 |
| 410 | 0.72 | 0.00 | 0.00 | 0.00 | 0.00 |
| 415 | 0.74 | 0.00 | 0.00 | 0.00 | 0.00 |
| 420 | 0.71 | 0.00 | 0.00 | 0.00 | 0.00 |
| 425 | 0.71 | 0.00 | 0.00 | 0.00 | 0.00 |
| 430 | 0.74 | 0.00 | 0.00 | 0.00 | 0.00 |
| 435 | 0.74 | 0.00 | 0.00 | 0.00 | 0.00 |
| 440 | 0.73 | 0.00 | 0.00 | 0.00 | 0.00 |
| 445 | 0.78 | 0.00 | 0.00 | 0.00 | 0.00 |
| 450 | 0.85 | 0.00 | 0.00 | 0.00 | 0.00 |
| 455 | 0.88 | 0.00 | 0.00 | 0.00 | 0.00 |
| 460 | 0.88 | 0.00 | 0.00 | 0.00 | 0.00 |
| 465 | 0.94 | 0.00 | 0.00 | 0.00 | 0.00 |
| 470 | 1.00 | 0.00 | 0.00 | 0.00 | 0.00 |
| 475 | 0.89 | 0.00 | 0.00 | 0.00 | 0.00 |
| 480 | 0.89 | 0.00 | 0.00 | 0.00 | 0.00 |
| 485 | 0.79 | 0.00 | 0.00 | 0.00 | 0.00 |
| 490 | 0.80 | 0.00 | 0.00 | 0.00 | 0.00 |
| 495 | 0.75 | 0.00 | 0.00 | 0.00 | 0.00 |
| 500 | 0.74 | 0.00 | 0.00 | 0.00 | 0.00 |
| 505 | 0.74 | 0.00 | 0.00 | 0.00 | 0.00 |
| 510 | 0.75 | 0.00 | 0.00 | 0.00 | 0.00 |
| 515 | 0.75 | 0.00 | 0.00 | 0.00 | 0.00 |
| 520 | 0.75 | 0.00 | 0.00 | 0.00 | 0.00 |
| 525 | 0.74 | 0.00 | 0.00 | 0.00 | 0.00 |
| 530 | 0.74 | 0.00 | 0.00 | 0.00 | 0.00 |
| 535 | 0.74 | 0.00 | 0.00 | 0.00 | 0.00 |
| 540 | 0.74 | 0.00 | 0.00 | 0.00 | 0.00 |
| 545 | 0.74 | 0.00 | 0.00 | 0.00 | 0.00 |

| | n=1 | n=2 | n=3 | n=4 | n=5 |
|---|---|---|---|---|---|
| m = 550 | 0.75 | 0.00 | 0.00 | 0.00 | 0.00 |
| 555 | 0.70 | 0.00 | 0.00 | 0.00 | 0.00 |
| 560 | 0.70 | 0.00 | 0.00 | 0.00 | 0.00 |
| 565 | 0.70 | 0.00 | 0.00 | 0.00 | 0.00 |
| 570 | 0.70 | 0.00 | 0.00 | 0.00 | 0.00 |
| 575 | 0.70 | 0.00 | 0.00 | 0.00 | 0.00 |
| 580 | 0.70 | 0.00 | 0.00 | 0.00 | 0.00 |
| 585 | 0.65 | 0.00 | 0.00 | 0.00 | 0.00 |
| 590 | 0.65 | 0.00 | 0.00 | 0.00 | 0.00 |
| 595 | 0.65 | 0.00 | 0.00 | 0.00 | 0.00 |
| 600 | 0.65 | 0.00 | 0.00 | 0.00 | 0.00 |
| 605 | 0.65 | 0.00 | 0.00 | 0.00 | 0.00 |
| 610 | 0.64 | 0.00 | 0.00 | 0.00 | 0.00 |
| 615 | 0.64 | 0.00 | 0.00 | 0.00 | 0.00 |
| 620 | 0.62 | 0.00 | 0.00 | 0.00 | 0.00 |
| 625 | 0.55 | 0.00 | 0.00 | 0.00 | 0.00 |
| 630 | 0.40 | 0.00 | 0.00 | 0.00 | 0.00 |
| 635 | 0.24 | 0.00 | 0.00 | 0.00 | 0.00 |
| 640 | 0.13 | 0.00 | 0.00 | 0.00 | 0.00 |
| 645 | 0.07 | 0.00 | 0.00 | 0.00 | 0.00 |
| 650 | 0.04 | 0.00 | 0.00 | 0.00 | 0.00 |
| 655 | 0.02 | 0.00 | 0.00 | 0.00 | 0.00 |
| 660 | 0.02 | 0.00 | 0.00 | 0.00 | 0.00 |
| 665 | 0.01 | 0.00 | 0.00 | 0.00 | 0.00 |
| 670 | 0.01 | 0.00 | 0.00 | 0.00 | 0.00 |
| 675 | 0.01 | 0.00 | 0.00 | 0.00 | 0.00 |
| 680 | 0.01 | 0.00 | 0.00 | 0.00 | 0.00 |
| 685 | 0.01 | 0.00 | 0.00 | 0.00 | 0.00 |
| 690 | 0.01 | 0.00 | 0.00 | 0.00 | 0.00 |
| 695 | 0.00 | 0.00 | 0.00 | 0.00 | 0.00 |

| | n=1 | n=2 | n=3 | n=4 | n=5 |
|---|---|---|---|---|---|
| m = 700 | 0.00 | 0.00 | 0.00 | 0.00 | 0.00 |
| 705 | 0.00 | 0.00 | 0.00 | 0.00 | 0.00 |
| 710 | 0.00 | 0.00 | 0.00 | 0.00 | 0.00 |
| 715 | 0.00 | 0.00 | 0.00 | 0.00 | 0.00 |
| 720 | 0.00 | 0.00 | 0.00 | 0.00 | 0.00 |
| 725 | 0.00 | 0.00 | 0.00 | 0.00 | 0.00 |
| 730 | 0.00 | 0.00 | 0.00 | 0.00 | 0.00 |
| 735 | 0.00 | 0.00 | 0.00 | 0.00 | 0.00 |
| 740 | 0.00 | 0.00 | 0.00 | 0.00 | 0.00 |
| 745 | 0.00 | 0.00 | 0.00 | 0.00 | 0.00 |
| 750 | 0.00 | 0.00 | 0.00 | 0.00 | 0.00 |
| 755 | 0.00 | 0.00 | 0.00 | 0.00 | 0.00 |
| 760 | 0.00 | 0.00 | 0.00 | 0.00 | 0.00 |
| 765 | 0.00 | 0.00 | 0.00 | 0.00 | 0.00 |
| 770 | 0.00 | 0.00 | 0.00 | 0.00 | 0.00 |
| 775 | 0.00 | 0.00 | 0.00 | 0.00 | 0.00 |
| 780 | 0.00 | 0.00 | 0.00 | 0.00 | 0.00 |
| 785 | 0.00 | 0.00 | 0.00 | 0.00 | 0.00 |
| 790 | 0.00 | 0.00 | 0.00 | 0.00 | 0.00 |
| 795 | 0.00 | 0.00 | 0.00 | 0.00 | 0.00 |
| 800 | 0.00 | 0.00 | 0.00 | 0.00 | 0.00 |
| 805 | 0.00 | 0.00 | 0.00 | 0.00 | 0.00 |
| 810 | 0.00 | 0.10 | 0.20 | 0.26 | 0.34 |
| 815 | 0.00 | 0.15 | 0.30 | 0.39 | 0.51 |
| 820 | 0.00 | 0.20 | 0.40 | 0.52 | 0.68 |
| 825 | 0.00 | 0.23 | 0.45 | 0.59 | 0.76 |
| 830 | 0.00 | 0.25 | 0.50 | 0.65 | 0.85 |
| 835 | 0.00 | 0.23 | 0.45 | 0.59 | 0.76 |
| 840 | 0.00 | 0.20 | 0.40 | 0.52 | 0.68 |
| 845 | 0.00 | 0.15 | 0.30 | 0.39 | 0.51 |
| 850 | 0.00 | 0.00 | 0.00 | 0.00 | 0.00 |

FIG. 8

| | r | g | b |
|---|---|---|---|
| Light Source Pattern 1 | 114 | 206 | 256 |
| Light Source Pattern 2 | 7 | 5 | 9 |
| Light Source Pattern 3 | 14 | 11 | 19 |
| Light Source Pattern 4 | 19 | 14 | 25 |
| Light Source Pattern 5 | 125 | 90 | 165 |

FIG.9

| $W_{i,m}$ | i=r | i=g | i=b |
|---|---|---|---|
| m = 400 | −0.0105 | −0.0015 | 0.0087 |
| 405 | −0.0101 | −0.0014 | 0.0084 |
| 410 | −0.0103 | −0.0015 | 0.0086 |
| 415 | −0.0105 | −0.0015 | 0.0088 |
| 420 | −0.0101 | −0.0014 | 0.0084 |
| 425 | −0.0100 | −0.0014 | 0.0084 |
| 430 | −0.0105 | −0.0015 | 0.0087 |
| 435 | −0.0105 | −0.0015 | 0.0088 |
| 440 | −0.0103 | −0.0015 | 0.0086 |
| 445 | −0.0111 | −0.0016 | 0.0093 |
| 450 | −0.0120 | −0.0017 | 0.0100 |
| 455 | −0.0125 | −0.0018 | 0.0105 |
| 460 | −0.0124 | −0.0018 | 0.0104 |
| 465 | −0.0133 | −0.0019 | 0.0111 |
| 470 | −0.0142 | −0.0020 | 0.0118 |
| 475 | −0.0127 | −0.0018 | 0.0106 |
| 480 | −0.0126 | −0.0018 | 0.0105 |
| 485 | −0.0113 | −0.0016 | 0.0094 |
| 490 | −0.0113 | −0.0016 | 0.0095 |
| 495 | −0.0106 | −0.0015 | 0.0088 |
| 500 | −0.0105 | −0.0015 | 0.0087 |
| 505 | −0.0105 | −0.0015 | 0.0087 |
| 510 | −0.0106 | −0.0015 | 0.0088 |
| 515 | −0.0107 | −0.0015 | 0.0089 |
| 520 | −0.0106 | −0.0015 | 0.0089 |
| 525 | −0.0105 | −0.0015 | 0.0088 |
| 530 | −0.0105 | −0.0015 | 0.0088 |
| 535 | −0.0105 | −0.0015 | 0.0088 |
| 540 | −0.0106 | −0.0015 | 0.0088 |
| 545 | −0.0106 | −0.0015 | 0.0088 |

| m | i=r | i=g | i=b |
|---|---|---|---|
| 550 | −0.0106 | −0.0015 | 0.0088 |
| 555 | −0.0099 | −0.0014 | 0.0082 |
| 560 | −0.0099 | −0.0014 | 0.0083 |
| 565 | −0.0099 | −0.0014 | 0.0083 |
| 570 | −0.0099 | −0.0014 | 0.0083 |
| 575 | −0.0099 | −0.0014 | 0.0083 |
| 580 | −0.0099 | −0.0014 | 0.0083 |
| 585 | −0.0092 | −0.0013 | 0.0077 |
| 590 | −0.0092 | −0.0013 | 0.0077 |
| 595 | −0.0093 | −0.0013 | 0.0077 |
| 600 | −0.0092 | −0.0013 | 0.0077 |
| 605 | −0.0092 | −0.0013 | 0.0076 |
| 610 | −0.0091 | −0.0013 | 0.0076 |
| 615 | −0.0091 | −0.0013 | 0.0076 |
| 620 | −0.0088 | −0.0013 | 0.0074 |
| 625 | −0.0078 | −0.0011 | 0.0065 |
| 630 | −0.0056 | −0.0008 | 0.0047 |
| 635 | −0.0033 | −0.0005 | 0.0028 |
| 640 | −0.0018 | −0.0003 | 0.0015 |
| 645 | −0.0010 | −0.0001 | 0.0008 |
| 650 | −0.0006 | −0.0001 | 0.0005 |
| 655 | −0.0003 | 0.0000 | 0.0003 |
| 660 | −0.0002 | 0.0000 | 0.0002 |
| 665 | −0.0002 | 0.0000 | 0.0001 |
| 670 | −0.0001 | 0.0000 | 0.0001 |
| 675 | −0.0001 | 0.0000 | 0.0001 |
| 680 | −0.0001 | 0.0000 | 0.0001 |
| 685 | −0.0001 | 0.0000 | 0.0001 |
| 690 | −0.0001 | 0.0000 | 0.0001 |
| 695 | −0.0001 | 0.0000 | 0.0001 |

| | i=r | i=g | i=b |
|---|---|---|---|
| m = 700 | −0.0001 | 0.0000 | 0.0000 |
| 705 | 0.0000 | 0.0000 | 0.0000 |
| 710 | 0.0000 | 0.0000 | 0.0000 |
| 715 | 0.0000 | 0.0000 | 0.0000 |
| 720 | 0.0000 | 0.0000 | 0.0000 |
| 725 | 0.0000 | 0.0000 | 0.0000 |
| 730 | 0.0000 | 0.0000 | 0.0000 |
| 735 | 0.0000 | 0.0000 | 0.0000 |
| 740 | 0.0000 | 0.0000 | 0.0000 |
| 745 | 0.0000 | 0.0000 | 0.0000 |
| 750 | 0.0000 | 0.0000 | 0.0000 |
| 755 | 0.0000 | 0.0000 | 0.0000 |
| 760 | 0.0000 | 0.0000 | 0.0000 |
| 765 | 0.0000 | 0.0000 | 0.0000 |
| 770 | 0.0000 | 0.0000 | 0.0000 |
| 775 | 0.0000 | 0.0000 | 0.0000 |
| 780 | 0.0000 | 0.0000 | 0.0000 |
| 785 | 0.0000 | 0.0000 | 0.0000 |
| 790 | 0.0000 | 0.0000 | 0.0000 |
| 795 | 0.0000 | 0.0000 | 0.0000 |
| 800 | 0.0000 | 0.0000 | 0.0000 |
| 805 | 0.0000 | 0.0000 | 0.0000 |
| 810 | 0.4050 | 0.4799 | −0.5665 |
| 815 | 0.6074 | 0.7198 | −0.8497 |
| 820 | 0.8099 | 0.9598 | −1.1330 |
| 825 | 0.9112 | 1.0797 | −1.2746 |
| 830 | 1.0124 | 1.1997 | −1.4162 |
| 835 | 0.9112 | 1.0797 | −1.2746 |
| 840 | 0.8099 | 0.9598 | −1.1330 |
| 845 | 0.6074 | 0.7198 | −0.8497 |
| 850 | 0.0000 | 0.0000 | 0.0000 |

ELECTRONIC ENDOSCOPE APPARATUS AND PROGRAM

BACKGROUND OF THE INVENTION

1. Field of the Invention

The present invention relates to an electronic endoscope apparatus for obtaining a color image of a target observation area by irradiating white illumination light thereon. More specifically, the invention relates to an electronic endoscope apparatus used in combination with a near infrared light irradiation unit that irradiates near infrared light on a target irradiation section. The invention also relates to a program for use with the electronic endoscope apparatus for generating a color image signal.

2. Description of the Related Art

Developments of optical tomographic image obtaining systems for obtaining optical tomographic images of living bodies and the like are under way. Well-known methods for obtaining optical tomographic images include the method using optical interference caused by frequency-swept coherent light, the method using optical interference caused by low coherence light, and the like.

In particular, an OCT (Optical Coherence Tomography) system that obtains an optical tomographic image by measuring a light intensity of low coherence interference light through heterodyne detection is put into practical use.

The OCT system obtains optical tomography information of a target measuring object through the steps of: splitting low coherence light outputted from a light source, which includes SLD (Super Luminescent Diode) or the like, into measuring light and reference light; slightly shifting the frequency of either the reference light or measuring light by a piezo device or the like; irradiating the measuring light on the target measuring object; causing interference between the reflected light reflected from the target irradiation section and the reference light; and measuring the optical intensity of the interference light through heterodyne detection as described, for example, in non-patent document "Real-time in vivo imaging of human gastrointestinal ultrastructure by use of endoscopic optical coherence tomography with a novel efficient interferometer design", A. M. Rollins et al., OPTICS LETTERS, Vol. 24, No. 19, pp. 1358-1360, 1999. By slightly changing the optical path length of the reference light through slight movement of a movable mirror or the like disposed in the optical path of the reference light, information at a predetermined depth of the target irradiation section where the optical path length of the reference light corresponds to the optical path length of the measuring light. Then, by repeating the measurement while slightly moving the section for irradiating the measuring light, an optical tomographic image of a predetermined area may be obtained.

The use of such OCT systems allow diagnosis of invasion depth of early cancer and the like, so that efforts for developing a method for obtaining an optical tomographic image within a body cavity by guiding measuring light and reflected light through the OCT probe insertable in a forceps channel of an endoscope apparatus are underway as described for example, in U.S. Pat. No. 6,668,185. The aforementioned patent publication describes an OCT system that includes an OCT probe having an optical fiber for guiding measuring light, and a mirror disposed at the distal end of the optical fiber and reflects the measuring light to an orthogonal direction. The OCT system displays a tomographic image of a wall of a body cavity by inserting the OCT probe into the body cavity through the forceps channel of the endoscope, and rotating the mirror disposed at the distal end of the probe.

Most of such OCT systems use near infrared light as the measuring light in order to reduce the optical loss at the target irradiation section. The near infrared light, however, is not visible, so that visible light, such as He—Ne laser, or the like is concentrically superimposed thereon and used as aiming light.

In the mean time, in the field of laser therapy systems, near infrared light, such as YAG laser or the like, is also used, and here again visible light is used as the aiming light.

Recently, in putting into practical use, the downsizing and simplified structure have been demanded for the near infrared light irradiation unit used in optical tomographic image obtaining systems and the like. In order to superimpose the aiming light concentrically with the near infrared light, however, it is necessary to dispose an optical device, such as a dichroic mirror or the like, or a coupler for combining the light or the like in the optical path. This causes a problem that the downsizing and simplified structure for the near infrared irradiation unit is prevented. On the other hand, the near infrared light irradiation unit without aiming light causes a problem that the section irradiated by the near infrared light is not visually recognized.

SUMMARY OF THE INVENTION

The present invention has been developed in view of the circumstances described above, and it is an object of the present invention to provide an electronic endoscope apparatus capable of displaying a section irradiated by the near infrared light within a color image in a visually recognizable manner, even when used in combination with a near infrared light irradiation unit without aiming light. It is a further object of the present invention to provide a program to be installed on an electronic endoscope apparatus used in combination with a near infrared light irradiation unit without aiming light for displaying a section irradiated by the near infrared light in a visually recognizable manner.

The endoscope apparatus of the present invention is an endoscope apparatus for use in combination with a near infrared light irradiation unit that irradiates near infrared light on a target irradiation section, the apparatus including:

an illumination means for irradiating white light, not including the near infrared light, on a target observation area including the target irradiation section;

an imaging means for spectroscopically imaging a reflected light image of the target observation area irradiated by the near infrared light and the white light, and outputting the image as a spectral image signal;

a storage section for storing estimated matrix data for estimating the reflected light intensity of the near infrared light;

an IR image signal generation means for generating an IR image signal constituted by an estimated value of the reflected light intensity of the near infrared light by performing a matrix operation on the spectral image signal using the estimated matrix data stored in the storage section and spectral matrix data of the near infrared light; and a color image signal generation means for generating a color image signal based on the spectral image signal and the IR image signal.

The estimated matrix data may be matrix data calculated based on spectral matrix data of a plurality of irradiation light patterns including the white light or the near infrared light, and pixel matrix data constituted by spectral image signals of the target observation area obtained by the imaging means using the plurality of irradiation light patterns.

The "pixel matrix data of spectral image signals of the target observation area" may be pixel matrix data of spectral image signals actually obtained by irradiating a plurality of irradiation light patterns including the white light or the near infrared light, on the target observation area prior to obtaining a color image thereof. In this case, the estimated matrix data are calculated immediately before obtaining the color image. The "pixel matrix data of the spectral image signal of the target observation area" may be pixel matrix data of spectral image signals obtained in advance by irradiating a plurality of irradiation light patterns including the white light or the near infrared light on an area which is a prospective candidate of the target observation area, such as esophageal wall, stomach wall, duodenal wall, or the like. In this case, the estimated matrix data are calculated and stored in advance, for example, prior to shipping the endoscope apparatus.

The estimated matrix data may be matrix data calculated based on spectral matrix data of a plurality of irradiation light patterns including the white light or the near infrared light, spectral characteristic data of the imaging means, and light reflection characteristic data of a visible light region and a near infrared light region of the target observation area. In this case, pixel matrix data of a target observation area may be obtained through an arithmetic operation, instead of actually irradiating a plurality of irradiation light patterns on the target observation area, and obtaining the pixel matrix data of spectral image signals of the target observation area.

The referent of "a plurality of irradiation light patterns including the white light or the near infrared light" as used herein may include: an irradiation light pattern of the white light alone; an irradiation light pattern of the near infrared light alone; an irradiation light pattern of combined light of the white and near infrared light combined at a predetermined ratio; and the like.

If the storage section includes a plurality of sets of estimated matrix data, each corresponding to each type of the target observation area, then the IR image signal generation means may be a means for calculating the IR image signal using estimated matrix data of the target observation area imaged by the imaging means among the plurality of sets of estimated matrix data.

If the spectral image signal obtained by the imaging means is constituted by a R (red) image signal, a G (green) image signal, and a B (blue) image signal, and at least one of the R (red) image signal, G (green) image signal, and B (blue) image signal includes a near infrared signal, then the color image signal generation means may be a means for generating a RGB color image signal based on a R color image signal which is based on the R (red) image signal, a G color image signal which is based on the G (green) image signal, and a B color image signal which is based on the B (blue) image signal and the IR image signal The color image signal generation means may be a means for generating a RGB color image signal based on a R color image signal which is based on the R (red) image signal, a G color image signal which is based on the G (green) image signal and the IR image signal, and a B color image signal which is based on the B (blue) image signal.

The near infrared light irradiation unit may be an optical tomogoraphic image obtaining apparatus that irradiates near infrared light on a target irradiation section, and obtains an optical tomographic image of the target irradiation section based on reflected light reflected from a predetermined depth of the target irradiation section.

The program of the present invention is a program for causing a computer to function as:

an IR image signal generation means for performing a matrix operation on a spectral image signal obtained by spectroscopically imaging a reflected light image of a target observation area irradiated by near infrared light and white light, not including the near infrared light, using estimated matrix data for estimating the image signal of the near infrared light and spectral matrix data of the near infrared light, and generating an IR image signal constituted by an estimated value of the light intensity of the near infrared light; and a color image signal generation means for generating a color image signal based on the spectral image signal and the IR image signal.

In the endoscope apparatus according to the present invention, estimated matrix data for estimating the reflected light intensity of the near infrared light are stored, then an IR image signal constituted by an estimated value of reflected light intensity of the near infrared light is generated by performing a matrix operation on the spectral image signal using the matrix data stored in the storage section and spectral matrix data of the near infrared light, and a color image signal is generated based on the spectral image signal of the target observation area and IR image signal. Thus, even when the endoscope apparatus is used in combination with a near infrared light irradiation unit without aiming light, the section irradiated by the near infrared light may be indicated within the displayed color image in a visually recognizable manner.

If the estimated matrix data are matrix data calculated based on spectral matrix data of a plurality of irradiation light patterns including the white light or the near infrared light, and pixel matrix data constituted by spectral image signals of the target observation area obtained by the imaging means using the plurality of irradiation light patterns, the pixel matrix data may be obtained easily and estimated matrix data may be calculated easily in advance or immediately before obtaining an optical tomographic image, so that the convenience of the endoscope apparatus is improved.

Further, if the estimated matrix data are data calculated based on spectral matrix data of a plurality of irradiation light patterns including the white light or the near infrared light, spectral characteristic data of the imaging means, and light reflection characteristic data of a visible light region and a near infrared light region of the target observation area, the estimated matrix data may be calculated only through an arithmetic operation without using a target observation area or a sample thereof, so that the time and effort required for calculating the estimated matrix data may be reduced.

If the storage section includes a plurality of sets of estimated matrix data, each corresponding to each type of the target observation area, and the IR image signal generation means is a means for calculating the IR image signal using estimated matrix data of the target observation area imaged by the imaging means among the plurality of sets of estimated matrix data, estimated matrix data appropriate for the type of the target observation area may be used, so that the near infrared light may be indicated more clearly in a visually recognizable manner.

If the spectral image signal obtained by the imaging means includes a R (red) image signal, a G (green) image signal, and a B (blue) image signal, and at least one of the R (red) image signal, G (green) image signal, and B (blue) image signal includes a near infrared signal, and if the color image signal generation means is a means that generates a RGB color image signal based on a R color image signal which is based on the R (red) image signal, a G color image signal which is based on the G (green) image signal, and a B color image signal which is based on the B (blue) image signal and the IR image signal, the near infrared light is displayed in pale blue, so that it is visually recognized with ease when displaying a color image of living body or the like.

The program according to the present invention may cause a computer to function as: an IR image signal generation means for performing a matrix operation on a spectral image signal obtained by spectroscopically imaging a reflected light image of a target observation area irradiated by near infrared light and white light, not including the near infrared light, using estimated matrix data for estimating the image signal of the near infrared light and spectral matrix data of the near infrared light, and generating an IR image signal constituted by an estimated value of the light intensity of the near infrared light; and a color image signal generation means for generating a color image signal based on the spectral image signal and IR image signal. Thus, for example, when an endoscope apparatus including the program of the present invention is combined with a near infrared irradiation unit without aiming light, the section irradiated by the near infrared light may be indicated within the displayed color image in a visually recognizable manner.

BRIEF DESCRIPTION OF THE DRAWINGS

FIG. 5 is a drawing for explaining spectral data of irradiation light.

FIG. 6 is a drawing for explaining spectral data of irradiation light.

FIG. 7 is a drawing for explaining spectral data of irradiation light.

FIG. 8 is a drawing for explaining a pixel matrix.

FIG. 9 is a drawing for explaining an estimated matrix.

FIG. 10 is a drawing for explaining an estimated matrix.

FIG. 11 is a drawing for explaining an estimated matrix.

DESCRIPTION OF THE PREFERRED EMBODIMENTS

Figure 1:
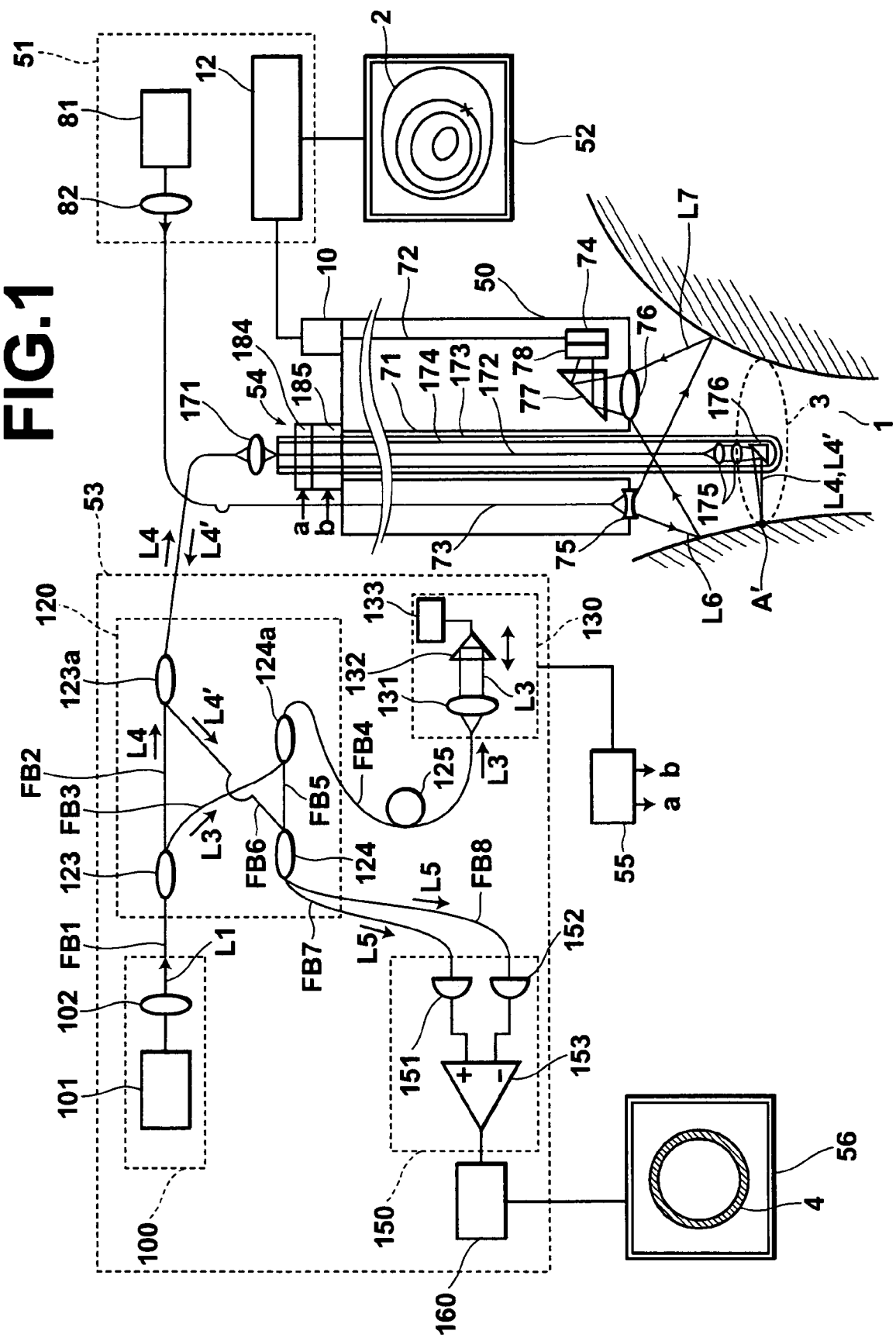
FIG. 1 is a schematic construction diagram of the electronic endoscope apparatus according to a first embodiment of the present invention.

Hereinafter, exemplary embodiments of the present invention will be described in detail with reference to the accompanying drawings. First, the electronic endoscope apparatus according to an embodiment will be described with reference to FIG. 1. The electronic endoscope apparatus is used in combination with an OCT apparatus (optical tomographic image obtaining apparatus) that obtains an optical tomographic image using 830 nm light.

The electronic endoscope apparatus includes: a main endoscope body that includes an insertion section 50, having a CCD imaging device 74 at the distal end, to be inserted into a body cavity 1 of a subject, and a CCD control section 10 connected to the insertion section 50; a processor apparatus 51, having a white light source 81 and a processor section 12, to which the main endoscope body is detachably attached; and a monitor 52 connected to the processor apparatus 51 and displays a color image.

The insertion section 50 includes a forceps channel 71 running therethrough. It further includes a CCD cable 72, and a light guide 73 extending to the distal end thereof. The CCD imaging device 74, having an on-chipped mosaic filter 78, is connected to the CCD cable 72 at the distal end thereof. An illumination lens 75 is provided at the distal end of the light guide 73, that is, the distal end section of the insertion section 50. The distal end section of the insertion section 50 further includes an imaging lens 76, and a prism 77 at the inner side of the imaging lens 76. The CCD imaging device 74 has sensitivity at least in the wavelength range of 400 to 850 nm.

Figure 3:
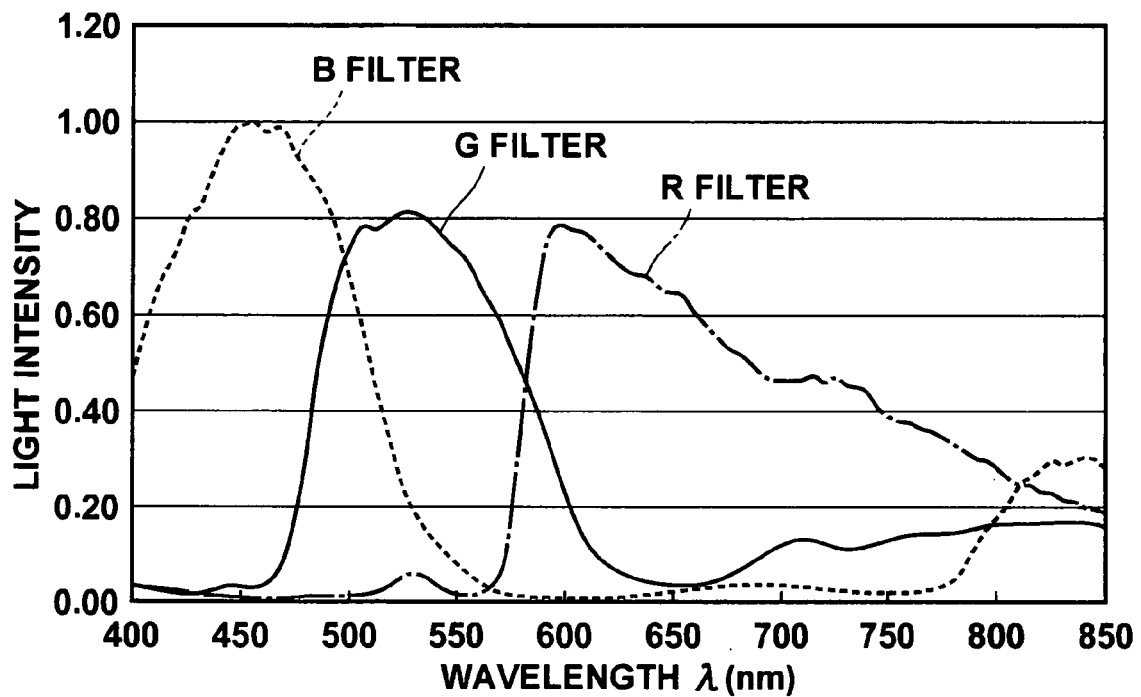
FIG. 3 is a drawing for explaining the mosaic filter shown in FIG. 1.

The mosaic filter 78 includes R filters that mainly transmit light in the red wavelength range, G filters that mainly transmit light in the green wavelength range, and B filters that mainly transmit light in the blue wavelength range, disposed in a mosaic pattern. FIG. 3 illustrates transmission characteristics of each type of the filters. As illustrated, each of the filters has certain light transmission characteristics adjacent to 830 nm.

The light guide 73 is connected to the white light source 81 disposed inside of the processor apparatus 51, and emits white light L6 used for obtaining an image of a target observation area. The white light source 81 emits white light, in which light having a wavelength greater than 700 nm is cut by a cut filter.

Figure 2:
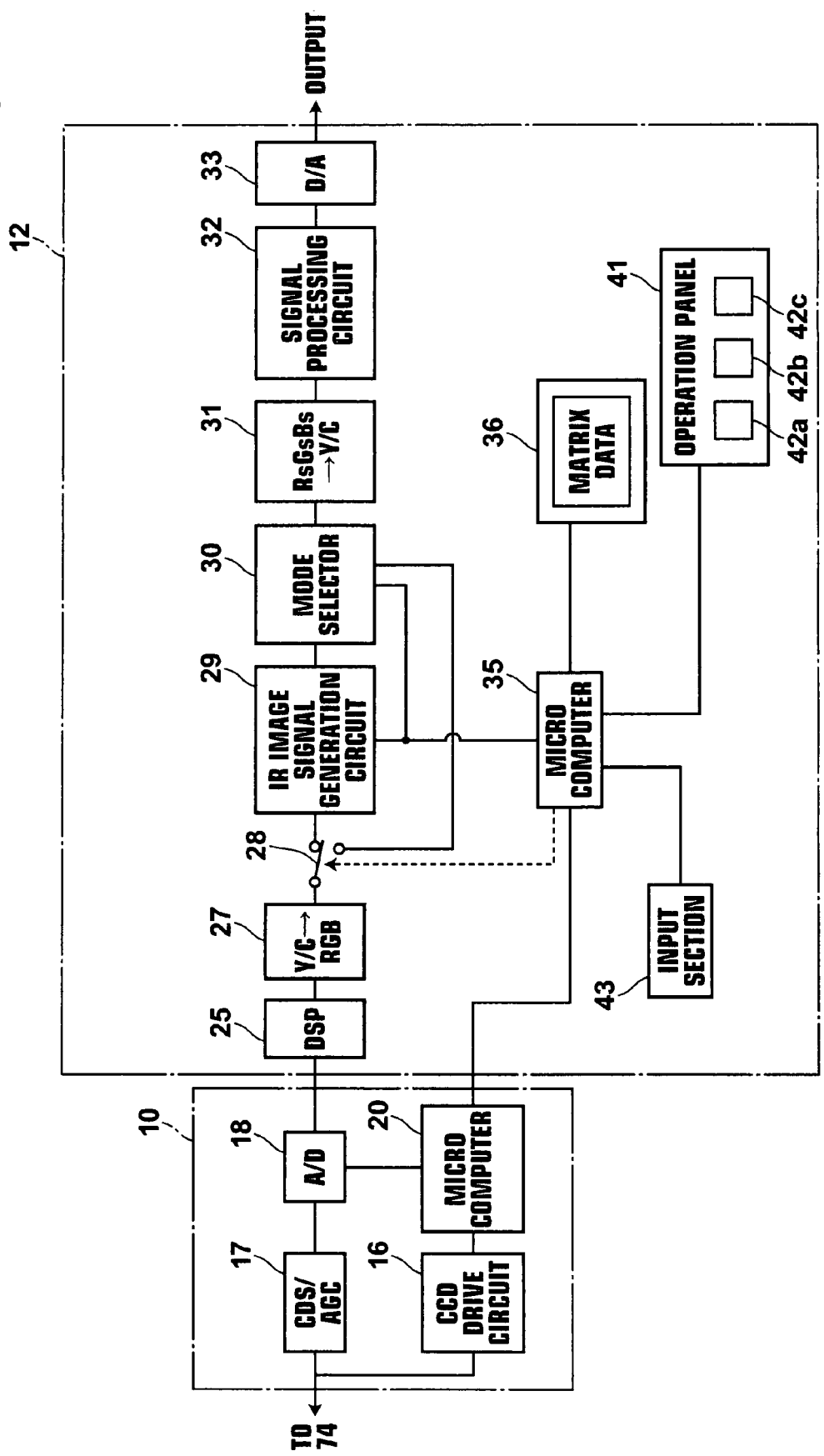
FIG. 2 is a schematic construction diagram of the CCD control section and processor section of the endoscope apparatus shown in FIG. 1.

The CCD cable 72 is connected to the CCD control section 10 which is connected to the insertion section 50. As illustrated in FIG. 2, the CCD control section includes: a CCD drive circuit 16 that generates a drive pulse based on a synchronization signal; a CDS/AGC (correlated double sampling/automatic gain control) circuit 17 that samples and amplifies an image (picture) signal outputted from the CCD imaging device 74; an A/D convert 18 that digitizes the analog signal outputted from the CDS/AGC circuit; and a microcomputer 20 that controls the circuits provided within the CCD control section, as well as controlling communication with the processor section 12.

The processor section 12 includes a DSP (digital signal processor) 25 that performs various types of image processing on the digitized image signal. The DSP 25 generates and outputs a Y/C signal including a luminance (Y) signal and a chrominance (C) signal. Note that the DSP 25 may be provided in the CCD control section 10. Connected to the DSP 25 is a first color conversion circuit 27 that converts the Y (luminance)/C (chrominance) signal outputted from the DSP 25 to three color (R, G, B) image signals. Connected to the first color conversion circuit 27 is a switcher 28. The switcher 28 outputs the inputted R, G, B signals to an IR image signal generation circuit 29, described later, if IR light image display mode is selected as the image display mode, or to a mode selector 30, described later, if normal image mode is selected.

The IR image signal generation circuit 29 performs a matrix operation on the R, G, B image signals to calculate an IR image signal that represents the intensity of reflected light L4' of measuring light L4 for OCT, described later, and outputs the IR image signal and R, G, B image signals to the mode selector 30 in the subsequent stage.

The mode selector 30 outputs the R, G, B signals inputted from the first color conversion circuit 27 directly to a second color conversion circuit 31 as Rs, Gs, and Bs signals used for generating a color image, if normal image mode is selected. If IR light image display mode is selected, it outputs the R and G image signals inputted from the IR image signal generation circuit 29 directly to the second color conversion circuit 31 as Rs and Gs signals, and as for the Bs signal, it outputs an image signal that includes the B signal and IR image signal inputted from the IR image signal generation circuit 29, superimposed with each other, to the second color conversion circuit 31.

In the second color conversion circuit 31, the inputted Rs, Gs, and Bs signals are converted to a Y/C signal and outputted to a signal processing circuit 32. In the signal processing circuit 32, various types of signal processing, such as mirror image processing, mask generation, character generation, and the like, are performed. The signal outputted from the signal processing circuit 32 is converted to an analog signal by a D/A converter 33, and outputted to the monitor 52.

The processor section 12 includes a microcomputer 35 that has functions to communicate with the CCD control section, to control each of the circuit provided within the processor section 12, to input matrix data for generating spectral data of irradiation light to the IR image signal generation circuit 29, and the like.

A memory 36 connected to the microcomputer 35 includes matrix data required for generating an IR image signal. A method for calculating the matrix data will now be described.

When a target observation area is imaged by a CCD device having R, G, B filters, values (r, g, b) of a pixel of the image is determined by the intensity and spectral distribution of the light incident on a position of the CCD device corresponding to the position of the pixel. For example, response vr obtained by a CCD element corresponding to a R filter, response vg obtained by a CCD element corresponding to a G filter, and response vb obtained by a CCD element corresponding to a B filter are represented by Formula (1) below.

$$v_i = \int_{400}^{850} t_i(\lambda) E(\lambda) S(\lambda) o(\lambda) d\lambda, i = r, g, b \quad (1)$$

where, tr ($\lambda$) is the spectral transmission of the R filter, tg ($\lambda$) is the spectral transmission of the G filter, tb ($\lambda$) is the spectral transmission of the B filter, E($\lambda$) is the spectral data of illumination light (spectral radiance), S($\lambda$) is the comprehensive spectral product including spectral transmission of the lens, spectral sensitivity of the CCD and the like, and O($\lambda$) is the spectral reflectance of the target observation area. Note that the spectral produce is assumed to be zero (0) other than in the range of 400 to 850 nm.

Here, an assumption is made in which illumination spectral data E ($\lambda$) is unknown, while others are known and substantially constant. In this case, an estimated matrix H for obtaining E ($\lambda$) is obtained in the following manner. First, color image signals are obtained using a plurality of different illumination light patterns, spectral data of which are known, and a pixel matrix V constituted by the pixel values of the color image signals.

The following five light source patterns are used as the illumination light patterns, and (rn, gm, and bm) are obtained for each pattern.

Light Source Pattern 1 (n=1): xenon white light source alone, denoted as Xe ($\lambda$) spectrum.

Light Source Pattern 2 (n=2): OCT measuring light alone, denoted as OCT ($\lambda$) spectrum.

Light Source Pattern 3 (n=3): light source combining the aforementioned two light sources (combination ratio, $a_1:b_1$), $a_1 \cdot Xe(\lambda) + b_1 \cdot OCT(\lambda)$ Light Source Pattern 4 (n=4): light source combining the aforementioned two light sources (combination ratio, $a_2:b_2$), $a_2 \cdot Xe(\lambda) + b_2 \cdot OCT(\lambda)$ Light Source Pattern 5 (n=5): light source combining the aforementioned two light sources (combination ratio, $a_3:b_3$), $a_3 \cdot Xe(\lambda) + b_3 \cdot OCT(\lambda)$ Hence, estimated illumination light spectral data $E_{est}$ may be expressed by Formula (2) below using the estimated matrix H and pixel matrix V.

$$E_{est} = HV \quad (2)$$

$$= H \begin{pmatrix} r_1 & \cdots & r_5 \\ g_1 & \cdots & g_5 \\ b_1 & \cdots & b_5 \end{pmatrix}$$

In the mean time, the illumination light spectral data E may be expressed by Formula (3) below.

$$HV \approx E \quad (3)$$

$$= \begin{pmatrix} e_{1,400} & \cdots & e_{5,400} \\ \vdots & \cdots & \vdots \\ e_{1,850} & \cdots & e_{5,850} \end{pmatrix}$$

$$= (Xe(\lambda) \ OCT(\lambda)) \begin{pmatrix} 1 & 0 & a_1 & a_2 & a_3 \\ 0 & 1 & b_1 & b_2 & b_3 \end{pmatrix}$$

Further, Formula 4 may be expanded like the following.

$$HV \approx E \quad (4)$$
$$HV\tilde{V} \approx E\tilde{V}$$
$$H(V\tilde{V})(V\tilde{V})^{-1} \approx E\tilde{V}(V\tilde{V})^{-1}$$
$$H = E\tilde{V}(V\tilde{V})^{-1}$$
$$= \begin{pmatrix} e_{1,400} & \cdots & e_{5,400} \\ \vdots & \cdots & \vdots \\ e_{1,850} & \cdots & e_{5,850} \end{pmatrix} \begin{pmatrix} r_1 & g_1 & b_1 \\ \vdots & \vdots & \vdots \\ r_5 & g_5 & b_5 \end{pmatrix}$$
$$\left[ \begin{pmatrix} r_1 & \cdots & r_5 \\ g_1 & \cdots & g_5 \\ b_1 & \cdots & b_5 \end{pmatrix} \begin{pmatrix} r_1 & g_1 & b_1 \\ \vdots & \vdots & \vdots \\ r_5 & g_5 & b_5 \end{pmatrix} \right]^{-1}$$

$\tilde{V}$ is the transposed matrix of V.

By substituting Formula (3) to Formula (4), the following estimated matrix H may be obtained.

$$H = \begin{pmatrix} w_{r400} & w_{g400} & w_{b400} \\ \vdots & \vdots & \vdots \\ w_{r625} & w_{g625} & w_{b625} \\ \vdots & \vdots & \vdots \\ w_{r850} & w_{g850} & w_{b850} \end{pmatrix} \quad (5)$$

Figure 4:
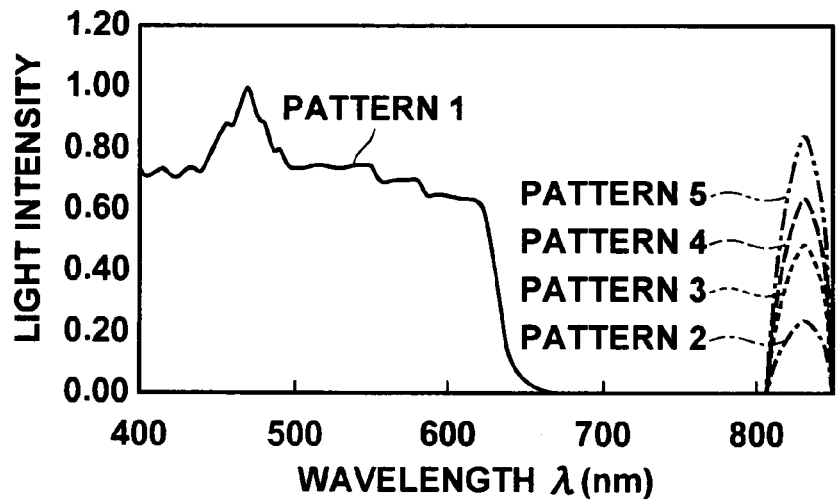
FIG. 4 is a drawing for explaining light source patterns.

For example, when five patterns shown in FIG. 4 are used as light source patterns, the illumination light spectral data E become a vector shown in FIGS. 5 to 7. FIG. 8 shows the pixel matrix V obtained by using a light source having these patterns. From the illumination light spectral data E shown in FIG. 5 to 7, and the pixel matrix V shown in FIG. 8, the estimated matrix H shown in FIGS. 9 to 11 may be obtained.

Accordingly, pixel values $WHV_{pixel\ data}$ of IR image signal, which is an image signal for indicating a section irradiated by the OCT measuring light, may be obtained by the following formula based on the estimated matrix H described above, a row vector W that represents light intensities of OCT measuring light at 5 nm intervals, and pixel values of image signal.

$$WHV_{pixel\ data} = \quad (6)$$

$$(k_{400} \cdots \cdots k_{625} \cdots \cdots k_{850}) \begin{pmatrix} w_{r400} & w_{g400} & w_{b400} \\ \vdots & \vdots & \vdots \\ w_{r625} & w_{g625} & w_{b625} \\ \vdots & \vdots & \vdots \\ w_{r850} & w_{g850} & w_{b850} \end{pmatrix} \begin{pmatrix} r_{pixel\ data} \\ \\ g_{pixel\ data} \\ \\ b_{pixel\ data} \end{pmatrix}$$

When SLD light having, for example, a center wavelength of 830 nm and Gaussian distribution with a full half bandwidth of 30 nm is used as the OCT measuring light, the row vector W may be expressed, for example, by the following formula.

$$W = (0, \ldots, 0, 0, 0.10, 0.15, 0.20, 0.23, 0.25, 0.23, 0.20, 0.15, 0.00)$$

805 810 815 820 825 830 835 840 845 850 nm

Further, if the OCT measuring light is 830 nm monochromatic light, Formula 6 may be expressed like the following.

$$WHV_{pixel\ data}$$

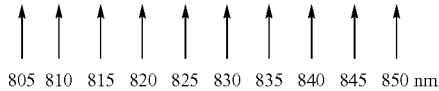

The memory 36 includes the row vector W and estimated matrix H. As for the estimated matrix, an estimated matrix H (esophagus) calculated through obtaining the pixel matrix V from an esophageal wall, an estimated matrix H (stomach) calculated through obtaining the pixel matrix V from a stomach wall, and an estimated matrix H (duodenum) calculated through obtaining the pixel matrix V from a duodenal wall are stored in advance.

Pixel values shown in Formula (6) are calculated by the IR image signal generation circuit 29. Therefore, an appropriate estimated matrix H is outputted to the IR image signal generation circuit 29 according to the type of the target observation area inputted by the user. At the same time, the row vector W for OCT measuring light is also inputted to the IR image signal generation circuit 29.

If a plurality of different types of OCT measuring light is provided, it is preferable that the row vector W and estimated matrix H are stored in the memory 36 for each type of the measuring light. If that is the case, an appropriate row vector and estimated matrix H are outputted to the IR image signal generation circuit 29 according to the type of a target observation area and the type of measuring light to be used in the actual measurement.

In addition to the memory 36, an operation panel 41 and an input section 43, which includes a keyboard and the like, are connected to the microcomputer 35. The operation panel 41 includes touch panels 42a to 42c for selecting a target observation area, as shown in FIG. 2.

The OCT apparatus includes: an OCT obtaining section for obtaining an optical tomographic image of a measuring region 3 within the body cavity 1; an OCT probe 54 inserted in the forceps channel 71 provided in the insertion section 50 of the electronic endoscope; an OCT control section 55 for controlling the operation for obtaining the optical tomographic image; and a monitor 56 for displaying the optical tomographic image 4.

The OCT obtaining section 53 includes: a light source section 100 for outputting low coherence light L1 having a center wavelength of 830 nm with a coherence length of 20 µm; a fiber coupling optical system 120 for splitting the low coherence light L1 into reference light L3 and measuring light L4, and for combining them; an optical path changing section 130, disposed in the optical path of the reference light L3, for changing the optical path length of the reference light L3; a balance difference detection section 150 for detecting the light intensity of interference light L5 between measuring light L4' reflected from a measuring point within the measuring region 3 and the reference light L3; and a signal processing section 160 for generating optical tomographic image data through heterodyne detection for obtaining the intensity of the measuring light L4' reflected from the measuring point within the measuring region 3 from the light intensity of the interference light L5 detected by the balance difference detection section 150.

The light source section 100 in the OCT obtaining section 53 includes an SLD (super Luminescent Diode) 101 for outputting the low coherence light L1, and a lens 102 for condensing the low coherence light L1 outputted from the SLD 101.

The fiber coupling optical system 120 includes a light splitting means 123, an optical circulator 123a, an optical circulator 124a, a wave combining means 124, and optical fibers FB1 to FB8.

The light splitting means 123 includes, for example, a 2×2 optical fiber coupler, and splits the low coherence light L1, guided thereto from the light source section 100 through the optical fiber FB1, into the measuring light L4 and reference light L3. The light splitting means 123 is optically connected to the two optical fibers FB2 and FB3, and the measuring light L4 is guided to the optical fiber FB2, while the reference light L3 is guided to the optical fiber FB3.

The optical fiber FB2 is optically connected to the OCT probe 54 through the optical circulator 123a. The OCT probe 54 is inserted into a body cavity through, for example, the forceps channel to guide the measuring light L4, guided through the optical fiber FB2, adjacent to the measuring region. The measuring light L4 outputted from the OCT probe 54 toward the measuring region 3 is reflected at the measuring region 3 and turned into the measuring light L4', which is inputted to the optical fiber FB6 through the optical circulator 123a.

In the mean time, the optical fiber FB3 is optically connected to the optical path length changing means 130 through the optical circulator 124a and the optical fiber FB4. The optical path length changing means 130 has a function to change the optical path length of the reference light L3, so that the measuring position within the measuring region 3 is changed in the depth direction. The reference light L3, changed in the optical path length by the optical path length changing means 130, is guided to the wave combining means 124 through the optical circulator 124a and the optical fiber FB5. The optical fiber FB4 includes a piezo device 125 for slightly shifting the frequency of the reference light L3.

The wave combining means 124, which includes a 2×2 optical fiber coupler, combines the reference light L3, changed in the optical path length by the optical path length changing means 130 and frequency shifted by the piezo device 125, with the measuring light L4' reflected from the measuring region 3, and outputs the interference light L5 between them to the balance difference detection section 150 through the optical fibers FB7 and FB8.

The optical path length changing means 130 includes: a prism 132, a lens 131 for collimating and outputting the reference light L3 outputted from the optical fiber FB4 to the prism 132, and inputting the reference light L3 reflected from the prism 132 to the optical fiber FB4; and a prism moving section 133 for moving the prism 132 in the horizontal directions in FIG. 1 to change the optical path length of the reference light L3. The prism moving section 133 operates under the control of the OCT control section 55.

The balance difference detection section 150 includes: optical detectors 151 and 152 for measuring the light intensity of the interference light L5; and a differential amplifier 153 for regulating the input balance between the value detected by the optical detector 151 and the value detected by the optical detector 152 to cancel out the noise and drift components, and then amplifying the difference.

The OCT probe 54 includes: a cladding tube 173 insertable into the forceps channel 71; a rotation sheath 174 inserted through the cladding tube 173 and rotatable with respect to the cladding tube 173; a fiber 172 inserted through the rotation sheath 174; a condenser lens system 175 fixed to the rotation sheath 174; and a prism 176, provided at the distal end section of the rotation sheath 174, which is ahead of the condenser lens system 175, for orthogonally reflecting the measuring light L4 and the measuring light L4'. The distal end section of the cladding tube 173 and the rotation sheath 174 is transparent to the measuring light L4. A centerless motor 184 for rotating the rotation sheath 174 and a probe moving section 185 are attached to the proximal end section of the cladding tube 173 and the rotation sheath 174.

The OCT control section 55 is connected to each component of the OCT obtaining section 53 to control the operation timing thereof as appropriate. Further, it controls the operation of the centerless motor 184 and probe moving section 185, thereby controlling the irradiation position of the measuring light L4 and rotation of the irradiation direction of the measuring light L4.

An operation of the electronic endoscope apparatus described above, which is a first specific embodiment of the present invention, will now be described. The observer inserts the insertion section 50 of the electronic endoscope apparatus into a body cavity of a subject and displays a target observation area image 2. Normally, that is, when not obtaining an optical tomographic image, normal image mode is set. First, the white light L6 outputted from the white light source 81 in the processor apparatus 51 is inputted to the light guide 73 through the lens 82 and guided to the distal end of the insertion section 50, then irradiated toward the body cavity 1 from the illumination lens 75. Reflected light L7 of the white light L6 is condensed by the imaging lens 76, then reflected by the prism 77, separated into each of color components by the mosaic filter 78, and focused on the CCD imaging device 74. The image signal obtained through photoelectric conversion by the CCD imaging device 74 is sampled and amplified by the CDS/AGC (correlated double sampling/automatic gain control) circuit 17 in the CCD control section 10. Then, the sampled and amplified image signal is digitized by the A/D converter 18, and outputted to the processor section 12.

In the processor section 12, the DSP (digital signal processor) 25 performs various types of image processing on the image signal, and outputs the image signal to the first color conversion circuit 27 after converting to a Y/C signal including luminance (Y) and chrominance (C) signals. In the first color conversion circuit 27, the Y (luminance)/C (chrominance) signal outputted from the DSP 25 is converted to R, G, B, three color image signals and outputted to the switcher 28. The switcher 28 outputs the R, G, B, three color signals to the mode selector 30, since normal mode is selected. The mode selector 30 outputs the R, G, B color signals inputted from the switcher 28 directly to the second color conversion circuit 31 as Rs, Gs, and Bs signals. In the second color conversion circuit 31, the inputted Rs, Gs, and Bs signals are converted to a Y/C signal and outputted to the signal processing circuit 32. In the signal processing circuit 32, various types of signal processing, such as mirror image processing, mask generation, character generation, and the like, are performed. The signal outputted from the signal processing circuit 32 is converted to an analog signal by the D/A converter 33 and outputted to the monitor 52.

The user inserts the OCT probe 54 into the forceps channel 71 of the insertion section 50, and moves the distal end of the insertion section 50, while monitoring the target observation area image 2 displayed on the monitor 52. When the distal end of the insertion section 50 reaches adjacent to the target section for obtaining an optical tomographic image, the user switches the image display mode to IR light image display mode, and causes low coherence L1 to be outputted from the light source section 100 of the OCT apparatus. Note that a configuration may be adopted in which the display mode is automatically switched to IR light image display mode when the low coherence light L1 is outputted. The user selects an intended type of target observation area, for example, esophageal wall, stomach wall, or duodenal wall, by depressing one of the touch panels 42a to 42c of the operation panel 41. The microcomputer 35 outputs an estimated matrix H and a row vector W for OCT measuring light corresponding to the selected type of the target observation area to the IR image signal generation circuit 29.

The low coherence light L1 is condensed by the lens 102 and inputted to the optical fiber FB1, which is guided through the optical fiber FB1, and spit into reference light 3 and measuring light 4 by the light spitting means 123. The measuring light L4 is guided through the optical fiber FB2 and optical circulator 123a, and inputted to the fiber 172 by the lens 171. The measuring light L1 outputted from the fiber 172 is condensed by the lens 175, and reflected by the prism 176 toward the body cavity 1 as spot light. The wavelength of the measuring light L4 is near 830 nm as described above, so that the section irradiated by the measuring light L4 is not visible by the naked eye.

In IR light image display mode, the R, G, B image signals outputted from the first color conversion circuit 27 are inputted to the IR image signal generation circuit 29 through the switcher 28. For each of the pixel values ($r_{pixel\ data}$, $g_{pixel\ data}$, $b_{pixel\ data}$) of R, G, B signals, the IR image signal generation circuit 29 calculates each pixel value $WHV_{pixel\ data}$ for IR image signal, which is an image signal for indicating an irradiated section by the OCT measuring light, based on formula (6) described above and estimated matrix H and row vector W for OCT measuring light. The IR image signal, formed of these pixel values, and R, G, B signals are outputted to the mode selector 30 in the subsequent stage.

Since IR light image display mode is selected, the mode selector 30 outputs the R and G image signals inputted from the IR image signal generation circuit 29 directly to the second color conversion circuit 31 as the Rs and Gs image signals, and as for the Bs signal, it outputs an image signal that includes the B signal and IR image signal inputted from the IR image signal generation circuit 29, superimposed with each other, to the second color conversion circuit 31.

In the second color conversion circuit 31, the inputted Rs, Gs, and Bs signals are converted to a Y/C signal and outputted to the signal processing circuit 32. In the signal processing circuit 32, various types of signal processing, such as mirror image processing, mask generation, character generation, and the like, are performed. The signal outputted from the signal processing circuit 32 is converted to an analog signal by a D/A converter 33, and outputted to the monitor 52.

The section irradiated by the measuring light L4 is indicated in blue within the color image 2 displayed on the monitor 52, so that it is visually recognized by the observer.

Next, an operation for obtaining an optical tomographic image 4 will be described. When obtaining an optical tomographic image, the observer determines the region for obtaining an optical tomographic image while monitoring a color image 2 displayed on the monitor 52.

In order to clarify the description, a measuring method for measuring optical tomographic information at a measuring point of a predetermined section within a measuring area to which the measuring light L4 is irradiated (target irradiation section) will be described first, and then the method for obtaining an optical tomographic image will be described. Low coherence light L1 outputted from the SLD 101 is split, by the light splitting means 123, into reference light L3 propagating toward the optical path length changing section 130 through the optical fiber FB3, and measuring light L4 propagating toward the OCT probe 54 through the optical fiber FB2. The reference light L3 is modulated by the piezo device 125 provided on the optical fiber FB4, thereby a slight frequency difference Δf is developed between the reference light L3 and measuring light L4.

The measuring light L4 is guided into the fiber 172 of the OCT probe 54 from the optical fiber FB2 through the optical circulator 123a. The measuring light outputted from the fiber 172 is irradiated on the target irradiation section within a body cavity 1 through the lens system 175 and prism 176. Measuring light L4', which is a portion of the measuring light L4 reflected from the surface and inside of the target irradiation section, is returned to the optical circulator 123a through the prism 176, lens system 175, fiber 172, and lens 171. The measuring light L4' returned to the optical circulator 123a is combined with the reference light L3 returned to the optical fiber FB4, described later, by the wave combining means 124.

In the mean time, the reference light L3 after modulated by the piezo device 125 is outputted to the prism 132 through the optical fiber FB4 and lens 131 of the optical path length changing section 130, which is reflected by the prism 132 and returned to the optical fiber FB4 again through the lens 131. The reference light L3 returned to the optical fiber FB4 is combined with the measuring light L4' by the wave combining means 124.

The measuring light L4' and reference light L3 combined by the wave combining means 124 are again coaxially superimposed with each other, and the measuring light L4' and reference light L3 interfere with each other when a predetermined condition is satisfied and turned into interference light L5 which generates a beat signal.

The reference light L3 and measuring light L4' are low coherence light L1 having a short coherence length, so that when the optical path length of the measuring light L4 (L4') to the wave combining means 124 corresponds to the optical path length of the reference light L3 to the wave combining means 124 after the low coherence light L1 is split into the measuring light L4 and reference light L3, i.e., if the measuring light L4' is reflected light reflected from the measuring point, interference occurs between them and a beat signal pulsating at a difference (Δf) in the frequency between them is generated. Note that the prism moving section 133 of the optical path length changing section 130 is controlled by the OCT control section 55 in advance such that the optical path length of the measuring light L4' reflected from an intended measuring point corresponds to the optical path length of the reference light L3.

The interference light L5 is split into two by the wave combining means 124, one of which is inputted to the optical detector 151 of the balance difference detection section 150 through the optical fiber FB 7, and the other of which is inputted to the optical detector 152 through the optical fiber FB8.

The optical detectors 151 and 152 detect the light intensity of the beat signal described above from the interference light L5. Then, the difference between a value detected by the optical detector 151 and a value detected by the optical detector 152 is obtained by the differential amplifier 153 and outputted to the signal processing section 160. The differential amplifier 153 has a function to adjust the balance of DC components between the input values. Therefore, even if a drift occurs in the low coherence light L1 outputted from the light source section 100, the difference between the input values may be amplified after adjusting the balance of the DC components, thereby the drift components are cancelled out and only the beat signal component is detected.

Through the operation process described above, tomography information of the target irradiation section at a predetermined depth within the body cavity 1 is obtained. While rotating the irradiation direction of the measuring light L4, by repeating the detection of the beat signal component every time the position of the measuring point orthogonal to the optical axis is moved by approximately 5 μm, information of the measuring points of the measuring region 3 equidistance from the rotation center of the irradiation direction of the measuring light L4, i.e., from the center of the prism 176 may be obtained at 5 μm intervals.

The OCT control section 55 controls the centerless motor 184 to rotate the prism 176 so that the irradiation direction of the measuring light L4 is rotated by 360 degrees. Then, the OCT control section 55 controls the prism moving section 133 to make the optical path length of the reference light L3 longer by 5 μm. In this state, information of the measuring point is obtained again at 5 μm intervals while rotating the irradiation direction of the measuring light L4, thereby information of the measuring points locating outside by 5 μm of the measuring points at A' shown in FIG. 1 may be obtained. If information of measuring points of 400 rotations is obtained at 5 μm intervals in the same manner as described above, information of the measuring points within the ring-shaped region with 2 mm thickness along the measuring region 3 may be obtained.

In the signal processing section 160, a heterodyne detection for obtaining the intensity of the measuring light L4' reflected at a predetermined plane of each of the measuring points from the light intensity of the interference light L5 detected by the balance difference detection section 150 is performed, which is then converted to an optical tomographic image and outputted to the monitor 56.

An optical tomographic image 4 of a sliced body cavity 1, shaped in a ring having a thickness of 2 mm like that shown in FIG. 1 is displayed on the monitor 56.

As clear from the description above, even if an optical tomographic image obtaining apparatus does not include aiming light, the section irradiated by the measuring light L4 is indicated in blue within a color image 2, so that the observer may visually recognize the section irradiated by the measuring light L4.

In the present embodiment, the description has been made of a case in which an electronic endoscope apparatus having a mosaic filter. But, it will be appreciated that the present invention is not limited to this, and may be applied to a frame sequential endoscope apparatus in which three filters are sequentially disposed in front of the CCD by rotation.

In the present embodiment, a pixel matrix V is obtained in advance through actual measurement, then an estimated matrix H is obtained based on the pixel matrix V, and the obtained estimated matrix is stored in the memory 36 in advance. If a comprehensive spectral product that combines optical reflectance of target observation area, wavelength transmission characteristics of each filter, spectral transmission of the lenses, spectral sensitivity of the CCD, and the like is known, the pixel matrix V may be obtained by formula (1), then the estimated matrix H is obtained based on the obtained pixel matrix V, and the obtained estimated matrix H is stored in the memory 36 in advance.

Alternatively, the pixel matrix V may be obtained by sequentially irradiating illumination light in light source patterns 1 to 5 prior to obtaining an optical tomographic image, then the estimated matrix H is calculated based on the obtained pixel matrix V, and the calculated estimated matrix H may be employed. As each value in the pixel matrix V, for example, an average value of the signal values obtained by all of the R filters, an average value of the signal values obtained by all of the G filters, an average value of the signal values obtained by all of the B filters, or the like may be used.

Further, in the present embodiment, RGB filters are used as the color filters, but complementary color filters may also be used.

Still further, in the present embodiment, the Bs image signal is created by adding the IR image signal to the B image signal for generating a RGB color image signal. Alternatively, the RGB color image signal may be generated by directly using the B image signal and R image signal as the Bs and Rs image signals, and creating the Gs signal by adding the IR image signal to the G image signal.

What is claimed is:

1. An endoscope apparatus for use in combination with a near infrared light irradiation unit that irradiates near infrared light on a target irradiation section, the apparatus comprising:
   an illumination means for irradiating white light, not including the near infrared light, on a target observation area including the target irradiation section;
   an imaging means for spectroscopically imaging a reflected light image of the target observation area irradiated by the near infrared light and the white light, and outputting the image as a spectral image signal;
   a storage section for storing estimated matrix data for estimating the reflected light intensity of the near infrared light;
   an IR image signal generation means for generating an IR image signal constituted by an estimated value of the reflected light intensity of the near infrared light by performing a matrix operation on the spectral image signal using the estimated matrix data stored in the storage section and spectral matrix data of the near infrared light; and
   a color image signal generation means for generating a color image signal based on the spectral image signal and the IR image signal.

2. The endoscope apparatus according to claim 1, wherein the estimated matrix data are calculated based on spectral matrix data of a plurality of irradiation light patterns including the white light or the near infrared light, and pixel matrix data constituted by spectral image signals of the target observation area obtained by the imaging means using the plurality of irradiation light patterns.

3. The endoscope apparatus according to claim 1, wherein the estimated matrix data are calculated based on spectral matrix data of a plurality of irradiation light patterns including the white light or the near infrared light, spectral characteristic data of the imaging means, and light reflection characteristic data of a visible light region and a near infrared light region of the target observation area.

4. The endoscope apparatus according to claim 1, wherein:
   the storage section includes a plurality of sets of estimated matrix data, each corresponding to each type of the target observation area; and
   the IR image signal generation means calculates the IR image signal using the estimated matrix data of the target observation area imaged by the imaging means among the plurality of sets of estimated matrix data.

5. The endoscope apparatus according to claim 2, wherein:
   the storage section includes a plurality of sets of estimated matrix data, each corresponding to each type of the target observation area; and
   the IR image signal generation means calculates the IR image signal using the estimated matrix data of the target observation area imaged by the imaging means among the plurality of sets of estimated matrix data.

6. The endoscope apparatus according to claim 3, wherein:
   the storage section includes a plurality of sets of estimated matrix data, each corresponding to each type of the target observation area; and
   the IR image signal generation means calculates the IR image signal using the estimated matrix data of the target observation area imaged by the imaging means among the plurality of sets of estimated matrix data.

7. The endoscope apparatus according to claim 1, wherein:
   the spectral image signal obtained by the imaging means is constituted by a R (red) image signal, a G (green) image signal, and a B (blue) image signal, and at least one of the R (red) image signal, G (green) image signal, and B (blue) image signal includes a near infrared signal; and
   the color image signal generation means generates a RGB color image signal based on a R color image signal which is based on the R (red) image signal, a G color image signal which is based on the G (green) image signal, and a B color image signal which is based on the B (blue) image signal and the IR image signal.

8. The endoscope apparatus according to claim 2, wherein:
   the spectral image signal obtained by the imaging means is constituted by a R (red) image signal, a G (green) image signal, and a B (blue) image signal, and at least one of the R (red) image signal. G (green) image signal, and B (blue) image signal includes a near infrared signal; and
   the color image signal generation means generates a RGB color image signal based on a R color image signal which is based on the R (red) image signal, a G color image signal which is based on the G (green) image signal, and a B color image signal which is based on the B (blue) image signal and the IR image signal.

9. The endoscope apparatus according to claim 3, wherein:
the spectral image signal obtained by the imaging means is constituted by a R (red) image signal, a G (green) image signal, and a B (blue) image signal, and at least one of the R (red) image signal, G (green) image signal, and. B (blue) image signal includes a near infrared signal; and
the color image signal generation means generates a RGB color image signal based on a R color image signal which is based on the R (red) image signal, a G color image signal which is based on the G (green) image signal, and a B color image signal which is based on the B (blue) image signal and the ER image signal.

10. The endoscope apparatus according to claim 1, wherein the near infrared light irradiation unit is an optical tomographic image obtaining apparatus that irradiates near infrared light on a target irradiation section, and obtains an optical tomographic image of the target irradiation section based on reflected light reflected from a predetermined depth of the target irradiation section.

11. The endoscope apparatus according to claim 2, wherein the near infrared light irradiation unit is an optical tomographic image obtaining apparatus that irradiates near infrared light on a target irradiation section, and obtains an optical tomographic image of the target irradiation section based on reflected light reflected from a predetermined depth of the target irradiation section.

12. The endoscope apparatus according to claim 3, wherein the near infrared light irradiation unit is an optical tomographic image obtaining apparatus that irradiates near infrared light on a target irradiation section, and obtains an optical tomographic image of the target irradiation section based on reflected light reflected from a predetermined depth of the target irradiation section.

* * * * *